US010488330B2

(12) United States Patent
Boonefaes

(10) Patent No.: US 10,488,330 B2
(45) Date of Patent: Nov. 26, 2019

(54) BUFFER-AND-SALT-CONTENT-INDEPENDENT UV-VIS SPECTROSCOPIC CHARACTERISATION OF SAMPLE DNA AND/OR RNA CONTENT USING REFERENCE SAMPLES HAVING DISTINCT BUFFER AND/OR SALT CONTENT

(71) Applicant: TRINEAN NV, Gentbrugge (BE)

(72) Inventor: Tom Boonefaes, Ghent (BE)

(73) Assignee: TRINEAN NV, Gentbrugge (BE)

( * ) Notice: Subject to any disclaimer, the term of this patent is extended or adjusted under 35 U.S.C. 154(b) by 922 days.

(21) Appl. No.: 14/424,570

(22) PCT Filed: Aug. 30, 2013

(86) PCT No.: PCT/EP2013/068011
§ 371 (c)(1),
(2) Date: Feb. 27, 2015

(87) PCT Pub. No.: WO2014/033268
PCT Pub. Date: Mar. 6, 2014

(65) Prior Publication Data
US 2015/0226664 A1  Aug. 13, 2015

(30) Foreign Application Priority Data

Aug. 30, 2012 (GB) .................... 1215484.5

(51) Int. Cl.
*G01N 21/33* (2006.01)
*C12Q 1/68* (2018.01)

(52) U.S. Cl.
CPC ............. *G01N 21/33* (2013.01); *C12Q 1/68* (2013.01); *G01N 2201/12* (2013.01); *Y10T 436/143333* (2015.01)

(58) Field of Classification Search
None
See application file for complete search history.

(56) References Cited

U.S. PATENT DOCUMENTS 10,126,233 B2  11/2018  Boonefaes
2012/0100547 A1  4/2012  Danker
2013/0332084 A1  12/2013  Boonefaes

FOREIGN PATENT DOCUMENTS

EP  2495546 A1  9/2012
WO  2004015136 A1  2/2004
WO  2012117036 A1  9/2012

OTHER PUBLICATIONS

Great Britain Search Report for corresponding Great Britain Application No. 1215484.5, dated Dec. 18, 2012.
International Search Report for corresponding International PCT Application No. PCT/EP2013/068011, dated Oct. 16, 2013.
Mach et al., "Detection of Proteins and Phenol in DNA Samples with Second-Derivative Absorption Spectroscopy," Analytical Biochemistry, Jan. 1, 1992, pp. 20-26, vol. 200, No. 1.
Montoye, "Specific RNA Quantification using cDrop: Comparison with UV Absorbance, the Ribogreen Fluorescent Assay and the Agilent Bioanalyser," Jul. 2011, URL:http://www.trinean.com/sites/trinean.com/files/documents/documents/AN%201.6%20Specific%20RNA%20quantification_0.pdf, retrieved Oct. 2, 2013.
Montoye,"Specific dsDNA Quantification UV/VIS-based cDrop Method vs. Picogreen Fluorescent Assay," 2011, URL:http://www.trinean.com/sites/trinean.com/files/documents/documents/AN%201.5%20Specific%20dsDNA%20quantification_cDrop%20VS%20picogreen%20fluorescent%20assay_0.pdf, retrieved Oct. 2, 2013.
Saurina et al.,"Procedure for the Quantitative Determination of Mixtures of Nucleic Acid Components Based on Multivariate Spectrophotometric Acid-Base Titrations," Analytical Chemistry, Jan. 1, 1999, pp. 126-134, vol. 71, No. 1.
Sodowich et al., "Method Validation of In Vitro RNA Transcript Analysis on the Agilent 2100 Bioanalyzer," Electrophoresis, 2007, pp. 2368-2378, vol. 28.

*Primary Examiner* — G Steven Vanni
(74) *Attorney, Agent, or Firm* — Cooley LLP

(57) ABSTRACT

A method is described for characterising a sample comprising at least DNA and/or RNA. The method comprises obtaining a UV-VIS spectroscopic measurement of the sample comprising at least DNA and/or RNA, deriving an absorption parameter based on the UV-VIS spectroscopic measurement, and determining a DNA and/or RNA quantification present in the sample. Determining a DNA and/or RNA quantification thereby comprises taking into account a buffer and/or salt effect on the UV-VIS spectroscopic measurement irrespective of the actual buffer and salt content of the sample, based on said derived absorption parameter and reference spectral data including spectral information for buffer and/or salt effects.

10 Claims, 3 Drawing Sheets

BUFFER-AND-SALT-CONTENT-INDEPENDENT UV-VIS SPECTROSCOPIC CHARACTERISATION OF SAMPLE DNA AND/OR RNA CONTENT USING REFERENCE SAMPLES HAVING DISTINCT BUFFER AND/OR SALT CONTENT

FIELD OF THE INVENTION

The invention relates to the field of detection and/or characterisation of DNA/RNA. More particularly, it relates to methods and systems for detection and/or characterisation of DNA and/or RNA containing samples through optical measurements of samples, such as through absorption or transmission measurements.

BACKGROUND OF THE INVENTION

Characterisation of samples is used in a wide variety of applications, such as for example in the field of biology, biotechnology, chemistry and for clinical and medical purposes. One increasingly popular class of samples that need to be characterised are samples containing DNA and/or RNA.

Although numerous analysis techniques for qualification and quantification of samples exists, only few analysis techniques are as simple to perform, fast and accurate as spectrophotometry. One example of spectrophotometry is UV-VIS absorbance spectroscopy. During such experiments, samples are irradiated with UV-VIS radiation of different wavelengths, the radiation remaining after passage through the sample is detected and the absorbance at different wavelengths is determined. As particular components will show a particular absorbance at particular wavelengths, such a particular absorbance profile can be used as a fingerprint which allows, upon comparison with reference spectra, to identify the components. When more complex samples are studied, the absorbance features in the spectrum can be significantly overlapping, rendering the interpretation of spectra substantially more difficult.

For obtaining the proper samples to be characterized with UV-VIS spectroscopy, currently, often different types of extraction methods are used. These DNA and/or RNA extraction methods use different reagents and in particular the final diluents may differ significantly in composition and/or buffering capacity from "standard" samples. The diluent is typically specifically optimized for optimal yield in an extraction process. These different reagents and diluents that are used for extracting the proper nucleic acid containing sample typically strongly influence the final conditions for these samples, resulting in usually unknown varying conditions. As these unknown varying conditions may strongly influence the characterisation results, it is required that these conditions are either taken into account or are compensated for. Especially if accurate quantification and spectral analysis is required at low levels of nucleic acids, taking into account these varying conditions is required, as in these cases the chemical condition, in which the measurement is done, has a significant impact on UV-VIS spectroscopic characterisation.

One solution that was exploited in the past was dilution of the sample with a suitable buffer for rendering more or less standard conditions. Nevertheless, this typically will introduce an additional step (reducing the convenience of the analysis and throughput thereof). More importantly this may introduce dilution errors.

In other solutions, the influence of the buffer conditions on the spectral characterisation were ignored, leading to inaccurate quantification of DNA and/or RNA content of samples, thereby rendering the technique at present a less trustworthy technique for characterizing DNA and/or RNA containing samples.

SUMMARY OF THE INVENTION

It is an object of embodiments of the present invention to provide good methods and systems for analysing DNA and/or RNA containing samples.

It is an advantage of embodiments according to the present invention that accurate quantification of DNA and/or RNA can be performed, irrespective of the buffering conditions.

It is an advantage of embodiments according to the present invention that the quantification of DNA and/or RNA can be performed such that it is less or not dependent on the sample conditions wherein the DNA and/or RNA is present.

It is an advantage of embodiments according to the present invention that the quantification of DNA and/or RNA can be performed such that it is less or not dependent on buffer concentrations and/or salt concentrations of the sample wherein the DNA and/or RNA is present.

It is an advantage of embodiments according to the present invention that the quantification of DNA and/or RNA can be performed without the need for bringing them under suitable conditions during loading or handling of the sample, e.g. while avoiding additional steps to be performed during said loading or handling.

It is an advantage of embodiments according to the present invention that compensation for effects of buffering conditions for the buffering of DNA and/or RNA during sample preparation can be performed automatically and/or in an automated way.

It is an advantage of embodiments according to the present invention that methods and systems can be provided wherein compensation for effects of buffering conditions can be performed by post-processing of the obtained UV-VIS spectrum, thus resulting in accurate results without the need for controlling buffer conditions, e.g. salt effects, of the DNA and/or RNA containing sample.

UV-Vis based quantification techniques traditionally discriminate DNA and RNA based on the ratio of the absorption at 260 nm to the absorption at 280 nm. Nevertheless, the effect of buffers and/or salts on this ratio can lead to an evolution of the A260/A280 ratio for RNA from 2.05 to lower than 1.8, a value which is accepted as being indicative for pure DNA. For embodiments, according to the present invention, it was surprisingly found that using a method and/or system taking into account spectral deformation due to buffer and/or salt effects allows for correctly discriminating RNA and DNA in mixtures at varying conditions. The above objective is accomplished by a method and device according to the present invention.

The present invention relates to a method for characterising a sample comprising at least DNA and/or RNA, the method comprising obtaining a UV-VIS spectroscopic measurement of the sample comprising at least DNA and/or RNA, and determining a DNA and/or RNA present in the sample, wherein said determining a DNA and/or RNA comprises taking into account a buffer and/or salt effect on the UV-VIS spectroscopic measurement irrespective of the actual buffer and salt content of the sample, based on reference spectral data including spectral information for buffer and/or salt effects. It is an advantage of embodiments according to the present invention that compensation for unwanted effects of buffers and/or salts on the UV-VIS spectroscopic measurement data of RNA and/or DNA can be obtained, based on reference spectral data and based on the UV-VIS spectroscopic measurement, irrespective of the buffer and/or salt concentration and in an automated and/or automatic way.

The method furthermore may comprise retrieving said reference spectral data including spectral information for buffer and/or salt contributions from a memory. It is an advantage of embodiments that the reference spectral data including spectral information for buffer and/or salt contributions can be stored, so that for a particular spectroscopic instrument type, the technique for taking into account buffer and/or salt contributions can be implemented in a software based manner, without the need for continuous measuring or for adjusting the buffering of the samples, prior to measuring.

Determining a DNA and/or RNA present may comprise using reference data representative for UV-VIS spectrophotometer data for at least two samples comprising DNA and/or RNA content and having distinct buffer and/or salt content. In other words, the reference spectral data including spectral information for buffer and/or salt effects may be or may be based on reference data representative for UV-VIS spectrophotometer data for at least two samples comprising DNA and/or RNA content and having distinct buffer and/or salt content.

At least part of the reference spectral data including spectral information for buffer and/or salt effects may be determined based on a method comprising obtaining prior information regarding DNA and/or RNA content and buffer and/or salt content for a plurality of samples having different buffer and/or salt content, obtaining UV-VIS spectrophotometer data for said samples, defining a number of overlapping components contributing in the UV-VIS spectrophotometer data, the number of overlapping components comprising one or more components assigned to RNA and/or DNA constituents of the one or more samples and the number of overlapping components comprising at least one component that cannot be assigned to known constituents of the one or more samples and that is considered representative of effects of buffer and/or salt effects on spectral contributions of RNA and/or DNA, and using the prior information for the one or more samples regarding their constituents and using the UV-VIS spectrophotometer data, estimating the constituents composition and the component contributions to the UV-VIS spectrophotometer data for the number of components for the one or more samples by minimizing a residue between the UV-VIS spectrophotometer data and a fit based on said constituent composition and said component contributions, thus obtaining information regarding the one or more components assigned to known constituents of the one or more samples and regarding the at least one component that cannot be assigned to known constituents of the one or more samples and that is considered representative of effects of buffer and/or salt effects on spectral contributions of RNA and/or DNA. It is an advantage of embodiments according to the present invention that a method for deriving the reference spectral data including spectral information for buffer and/or salt effects can be determined using a particular algorithm, resulting in a standard way for determining such information.

At least part of the reference spectral data including spectral information for buffer and/or salt effects may be determined based on a method comprising obtaining UV-VIS spectrophotometer data for at least two samples comprising DNA and/or RNA content and having distinct buffer and/or salt content, determining a difference spectrum based on the UV-VIS spectrophotometer data for the at least two samples, and determining at least part of the reference spectral data based on said difference spectrum.

The reference spectral data including spectral information for buffer and/or salt effects may represent a non-linear curve.

The sample may comprise RNA and quantifying may comprise quantifying an amount of RNA in the sample.

The present invention also relates to a system for characterising a sample comprising at least DNA and/or RNA, the system comprising an input means for obtaining a UV-VIS spectroscopic measurement of the sample comprising at least DNA and/or RNA, and a processor for determining a DNA and/or RNA present in the sample based on the obtained UV-VIS spectroscopic measurement, the processor being adapted for determining a DNA and/or RNA taking into account a buffer and/or salt effect on the UV-VIS spectroscopic measurement, irrespective of the actual buffer and salt content of the sample, based on reference spectral data including spectral information for buffer and/or salt effects.

The system may be adapted for performing a method as described herein.

The present invention also relates to the use of a method as described herein for quantifying an amount of RNA in a sample.

The present invention also relates to the use of a method as described herein, for determining a fraction of RNA in an RNA/DNA mixture in a sample.

The present invention also relates to a computer program product for, if implemented on a processing unit, performing a method as described herein.

The present invention also relates to a method for upgrading a spectrophotometer, the method comprising storing reference spectral data including spectral information for buffer and/or salt effects on a memory in a processor of the spectrophotometer, and installing a computer program product as described herein on the spectrophotometer system.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
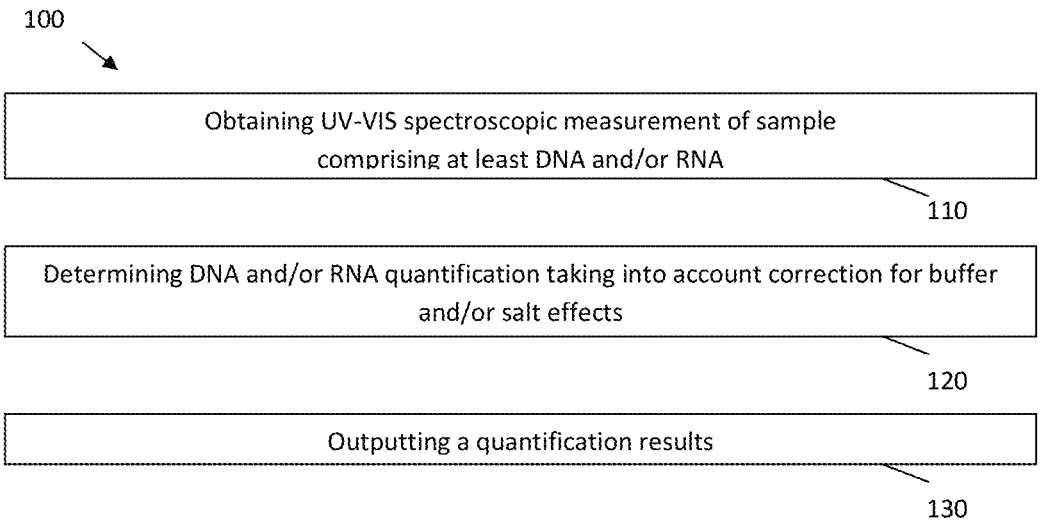
FIG. 1 illustrates an exemplary method for characterizing DNA and/or RNA comprising samples according to an embodiment of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operating in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Embodiments of the present invention can be used in methods and systems for optical characterisation. Such optical characterisation may typically be UV-VIS spectrophotometry. Where reference is made to UV-VIS, reference is made to a wavelength region having an upper wavelength in the region 300 nm to 1100 nm and a lower wavelength in the region 150 nm to 299 nm. Characterisation of microvolume samples using microfluidic devices may comprise detection of the presence of certain components, determination of concentration of certain components, determination of certain reactions occurring, etc. Such characterisation may include for example applications in the field of biology, biotechnology, chemistry, the clinical field and/or the medical field.

Where in embodiments of the present invention reference is made to samples comprising at least DNA and/or RNA, reference may for example be made to samples comprising DNA, double stranded DNA and/or RNA. Such samples typically are built up of nucleotides, which can be based on different nitrogeneous bases being adenine, thymine, guanine, cytosine and/or uracil.

Where in embodiments of the present invention reference is made to samples comprising "buffers and/or salts" or "a buffer and/or salt content", the latter typically may refer to buffer and/or salt components introduced for extracting DNA and/or RNA. Buffers and/or salts may define a pH of the sample in the range 5.5 to 8.5, advantageously in the range 7.0 to 8, although, according to embodiments of the present invention, the pH of the sample also may vary outside this range and according to embodiments of the present invention effects of pH on the spectral data obtained can be taken into account for determining a quantification of DNA and/or RNA. Buffer solutes may for example be soluble electrolytes or buffer salts. The buffer solute may comprise any or a combination of sodium-chloride, potassium-chloride, sodium-citrate, Tris.HCl, potassium phosphate or sodium phosphate, although embodiments of the present invention are not limited thereby.

In a first aspect, the present invention relates to a method for characterising a sample comprising at least DNA and/or RNA. Whereas the method is especially suitable for quantifying RNA, the latter is not limited thereto. According to an embodiment of the present invention, the method comprises obtaining a UV-VIS spectroscopic measurement of the sample comprising at least DNA and/or RNA. The latter may be done using any suitable UV-VIS spectrometer, allowing to collect spectrometer data. For RNA and DNA, the spectral region of interest advantageously includes the range 230 nm to 340 nm, although embodiments of the present invention are not limited thereto. Further according to an embodiment of the present invention, the method comprises determining DNA and/or RNA present in the sample. In some embodiments, quantification of the DNA and/or RNA presence in the sample is performed. During such determining, buffer and/or salt effects on the UV-VIS spectroscopic measurement is taken into account irrespective of the actual buffer and salt content of the sample, based on reference spectral data including information regarding buffer and/or salt effects. In other words, irrespective of the actual buffer and/or salt content of the sample, significant contributions or substantially the whole effect of deformation and/or shift caused by the presence of buffer and/or salt content is compensated for, so that this avoids erroneous quantification. Such reference spectral data including information regarding buffer and/or salt effects may in one example be embedded in different reference spectra of DNA and/or RNA for different buffer and/or salt contents used for fitting the obtained spectral data. Alternatively, a spectrum that directly is representative for the buffer and/or salt effects can also be used.

By way of illustration, embodiments of the present invention not being limited thereto, an example of a method according to an embodiment will be further described with reference to FIG. 1, illustrating some standard and optional features.

FIG. 1 illustrates an exemplary method 100 for characterizing DNA and/or RNA in a sample comprising DNA and/or RNA. The method more particularly is especially suitable for quantifying an amount of DNA and/or RNA present in a sample, and for providing an accurate quantification of DNA and/or RNA little subject or even independent of the buffer concentration or salt concentration used.

In a first step 110, the method 100 for characterizing DNA and/or RNA in a sample comprising DNA and/or RNA comprises obtaining a UV-VIS spectroscopic measurement of the sample comprising at least DNA and/or RNA. The step typically may comprise recording a spectrum, e.g. using a spectrophotometer, although the step also may be a step of receiving previously recorded spectrophotometer measurement data stored in a memory or inputted via an input channel. Typically such a spectrum will comprise spectral data in at least a range 230 nm to 340 nm, which is the region wherein the contribution of RNA and/or DNA is typically large, but depending on the application, spectral data from another range may also be used.

In a second step 120, the method 100 comprises determining a DNA and/or RNA quantification of the DNA and/or RNA present in the sample. Such quantification may include a full quantification or it may comprise determining a ratio of DNA to RNA, etc. As indicated above, according to embodiments of the present invention, such a quantification takes into account a buffer and/or salt effect on the UV-VIS spectroscopic measurement irrespective of the actual buffer and salt content of the sample, based on reference spectral data including information regarding buffer and/or salt effects. The method may therefore, in some embodiments, comprise the step of obtaining reference spectral data directly representative for buffer and/or salt effects. The latter can be performed in a plurality of ways.

Figure 2:
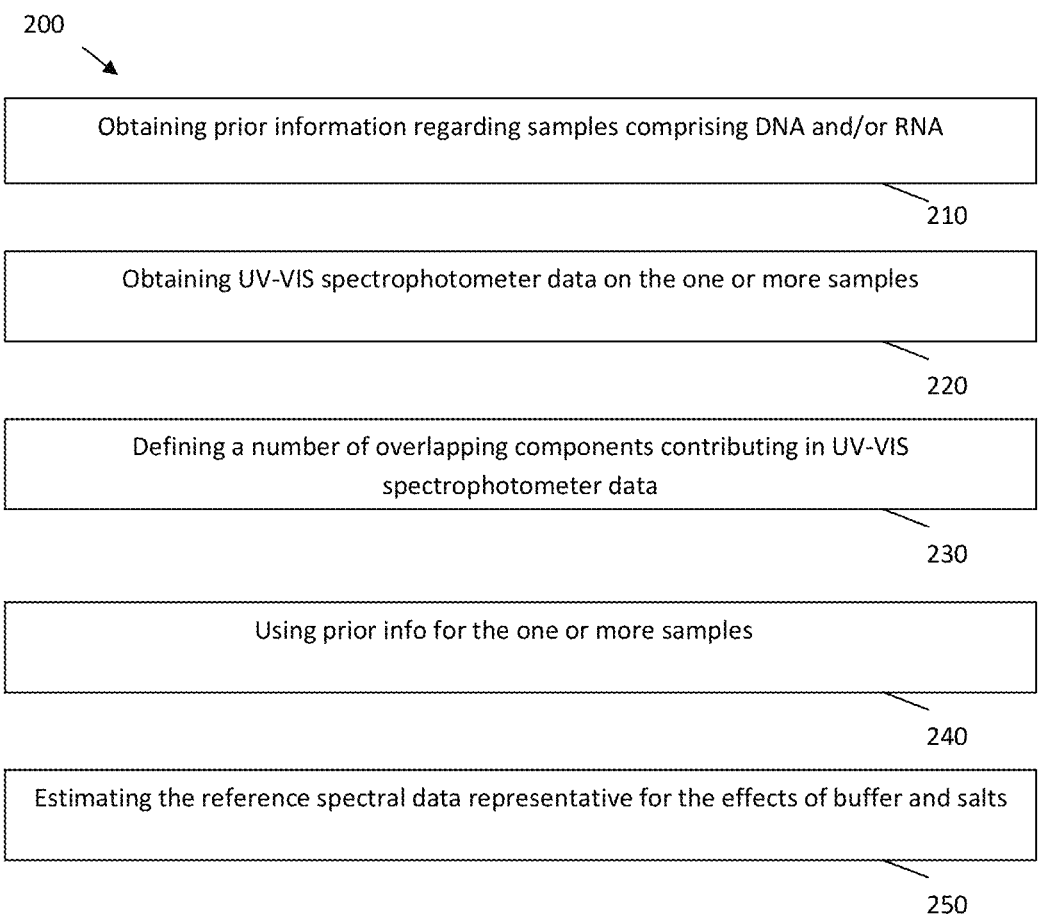
FIG. 2 illustrates a method for obtaining reference spectroscopic data including spectral information regarding deformation and/or shift due to buffers and/or salts, as can be used in an embodiment according to the present invention.

Either previously determined information that has been stored may be received from a memory. Alternatively or in addition thereto, in one example, obtaining reference spectral data including spectral information for buffer and/or salt effects may be obtained according to a predetermined algorithm. By way of illustration, the present invention not being limited thereto, an example of obtaining the information according to a predetermined algorithm is shown in FIG. 2.

According to the predetermined algorithm, reference spectral data including spectral information for buffer and/or salt effects can for example be determined as follows: The particular algorithm may comprise the following steps:

First, obtaining 210 prior information for the one or more samples regarding their constituents is performed. In one example a dilution array can be used, and the different samples may be samples comprising the same DNA and/or RNA content for different dilutions, thus resulting in different relative concentrations with respect to buffers and salts. Such prior information for the one or more samples regarding their constituents may comprise in some embodiments one or more reference spectra, e.g. for DNA and/or RNA or its components. Such prior information alternatively or in addition thereto also may comprise expected composition information, such as for example expected concentrations, expected ratios between different constituents, etc. In some embodiments a combination of such prior information also can be used.

The algorithm also comprises obtaining 220 UV-VIS spectrophotometer data for the one or more samples. Such UV-VIS spectrophotometer data typically may be a spectrophotometer spectrum, although information at one or more individual wavelengths or wavelength ranges also may be used.

The method according to the present invention also comprises defining 230 a number of overlapping components contributing in the UV-VIS spectrophotometer data, the number of overlapping components comprising one or more components assigned to RNA and/or DNA constituents of the one or more samples and the number of overlapping components comprising at least one component that cannot be assigned to known constituents of the one or more samples and that is considered representative of effects of buffer and/or salt effects on spectral contributions of RNA and/or DNA.

The method further comprises using 240 the prior information for the one or more samples regarding their constituents and using the UV-VIS spectrophotometer data, estimating 250 the constituents composition and the component contributions to the UV-VIS spectrophotometer data for the number of components for the one or more samples by minimizing a residue between the UV-VIS spectrophotometer data and a fit based on said constituent composition and said component contributions, thus obtaining information regarding the one or more components assigned to known constituents of the one or more samples and regarding the at least one component that cannot be assigned to known constituents of the one or more samples and that is considered representative of effects of buffer and/or salt effects on spectral contributions of RNA and/or DNA (i.e. obtaining the reference spectral data).

Alternatively to obtaining a reference spectrum directly representative for buffer and/or salt effects, the quantification can take into account a buffer and/or salt effect on the UV-VIS spectroscopic measurement irrespective of the actual buffer and salt content of the sample, by using for the fitting of the DNA and/or RNA contributions, different reference spectra of DNA and/or RNA for different buffer and/or salt contents used for fitting the obtained spectral data. Reference spectra may be previously obtained, calibrated during use, stored in a memory, etc.

The method also may comprise repeating the estimating step and fitting step e.g. for further minimizing the total residue by iteratively applying these steps. Such iteration process may be performed until the remaining residue between the UV-VIS spectrophotometer data and the fit based on the constituent composition is smaller than a predetermined value, or until a maximum number of iteration steps would be reached. The predetermined value referred to may be based on predetermined rules, based on a neural network, based on predetermined algorithms, based on information regarding the one or more samples, etc. In some embodiments, minimization of the residue may only be performed for those samples that have the smallest residue, allowing obtaining more accurate results and/or quicker convergence.

The method in one embodiment may allow providing as an output information a reference spectrum for a buffer and/or salt effect. The latter can be used for setting up a library of different reference spectra compatible with different constituents or effects thereof.

By way of illustration, the algorithm comprising a number of particular steps will be described using a particular mathematical matrix formalism, although embodiments of the present invention are not limited thereto another mathematical formalism also may be used.

For illustrating the algorithm, a number of definitions first are provided:

A: represents measurement data (expressed in absorbances, OD 10 mm) of a plurality of samples having known DNA and/or RNA concentration, typically measured in a wavelength range comprising 250 nm to 340 nm, e.g. in the range 230 nm and 400 nm.

A set of samples can for example be obtained from a dilution array, whereby a sample comprising DNA and/or RNA is diluted using different solvents. The latter results in the presence of different concentrations of buffer and salt content.

Q: represents the relative presences of the different known components being DNA and RNA or constituents thereof and at least one unknown constituent, being the component corresponding with deformation and/or shift of the DNA and/or RNA spectrum due to buffer and salt content.

R: represents the reference spectra, whereby a plurality of spectra are considered known being the spectra for DNA and/or RNA or constituents thereof, whereas also at least one unknown spectral component is present, being the spectral component corresponding with the deformation and/or shift of the DNA and/or RNA spectrum due to buffer and salt content.

The following expression then is valid between the components, the coefficient matrix and the measurement matrix:

$$RQ=A \quad [1]$$

By transposing the entire equation [1] the following relation is obtained.

$$Q^T \cdot R^T = A^T \quad [2]$$

and the reference spectra can be found by $$R^T = pinv(Q^T) \cdot A^T \quad [3]$$

For the dilution array of samples, the coefficients of a number of subcomponents are known, whereas the coefficient of the unknown component is not known yet. Similar, the reference spectra for the known components are considered known, whereas this is not the case for the reference spectrum for the component representative of the effects of buffers and salts. In order to extract the reference spectrum for the component representative of the effects of buffers and salts, in the present example the following recursive algorithm is performed:

First an estimation is made for the component contributions R, which in the present example is done using the following steps:

Using the knowledge of the dilution array and the measurement results, the matrix A is filled, and the matrix Q expressing the coefficients of the components is filled. For the known components this can be based on prior knowledge, for the unknown component representative of the effect of buffer and salt content, this may be by making use of an initialization value.

Using Q and A, the reference matrix R can be determined, taking into account that part of R may be known already. Such determination can be based on equation [3]. After the unknown component contribution in R is estimated, the coefficients (composition information) are recalculated based on the first estimation of the component contribution in R, in the present done by performing the following steps Calculate the predicted spectra (S) and determine the concentrations based on the components being present, as expressed by equation [4]

$$Q^T = pinv(R^T) \cdot A^T \quad [4]$$

Thereafter a new estimation of the components contribution R is determined, in the present example using the determined concentrations and re-calculating the new reference spectra.

Determination of the estimation of the composition information and the components contribution can be done by iteration until Q and R converge (which seems to be the case).

The above determination gives one example for determining reference spectra, but embodiments of the present invention are not limited thereto and reference data generated in another way also may be applied.

In an alternative method, at least part of the reference spectral data including information for buffer and/or salt effects are reference spectral data of two samples having different, e.g. extreme, buffer and/or salt concentrations. The latter may for example be used as follows. The algorithm may comprise obtaining UV-VIS spectrophotometer data for at least two samples comprising DNA and/or RNA content and having distinct buffer and/or salt content, and using such data for fitting the UV-VIS spectrophotometer data for deriving the actual contribution of DNA and/or RNA, substantially independent from the buffer and/or salt content.

In still another alternative, a difference spectrum determined based on spectral data for at least two samples comprising DNA and/or RNA content and having distinct buffer and/or salt content can be used.

In yet a further method of the method for characterizing DNA and/or RNA, the method may comprise outputting 130 a quantification result.

Embodiments according to methods of the present invention may be implemented as software as well as hardware.

Figure 3:
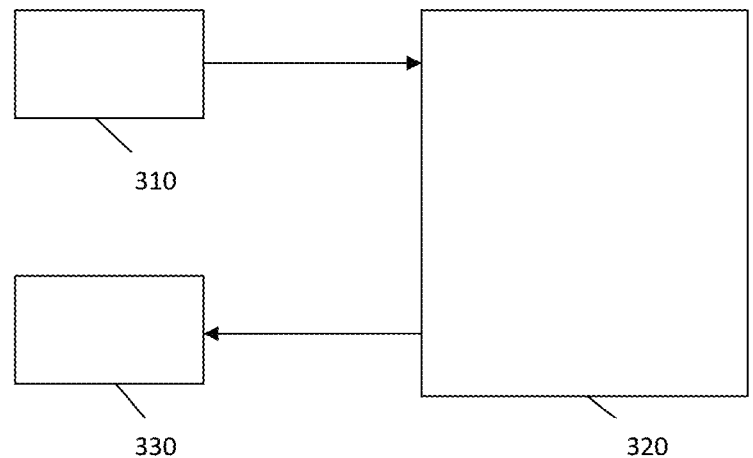
FIG. 3 illustrates a system for characterizing DNA and/or RNA comprising sample, according to an embodiment of the present invention.

In another aspect, the present invention also relates to a system for characterising a sample comprising at least DNA and/or RNA. The system comprises an input means for obtaining a UV-VIS spectroscopic measurement of the sample comprising at least DNA and/or RNA. The latter may be an input port for receiving prior information and spectrophotometer data. Alternatively the input means may also comprise a measurement system for recording UV-VIS spectrophotometer data such as for example a spectrophotometer. The system furthermore comprises a processor programmed for determining a DNA and/or RNA quantification present in the sample based on the obtained UV-VIS spectroscopic measurement, the processor being adapted for determining a DNA and/or RNA quantification taking into account a buffer and/or salt effects on the UV-VIS spectroscopic measurement irrespective of the actual buffer and salt content of the sample, based on reference spectral data including spectral information for buffer and/or salt effects. Such a processing means may be for example a CPU although embodiments of the present invention are not limited thereto. The system furthermore may be equipped with an output means for outputting information determined using the processing means, such as e.g. a memory, a display, a printer or a plotter. By way of illustration, a system for characterizing a sample 300 comprising an input means 310, a processor 320 and an output means 330 is shown in FIG. 3.

In another aspect, the present invention relates to a method for upgrading a spectrophotometer system. The method for upgrading typically may comprise storing reference spectral data including spectral information for buffer and/or salt effects, or deriving such data using the spectrophotometer system. The method for upgrading furthermore may comprise providing a measurement protocol implementing a method for characterizing DNA and/or RNA according to an embodiment of a method as described above. Such a method for upgrading may be applied to existing spectrophotometer systems, whereby, through software implementation, the system can be altered to have the benefits of systems or methods as described above.

In still another aspect, embodiments of the present invention also relate to computer-implemented methods for performing at least part of the methods for characterizing DNA and/or RNA in a sample comprising at least DNA and/or RNA. The methods may be implemented in a computing system. They may be implemented as software, as hardware or as a combination thereof. Such methods may be adapted for being performed on computer in an automated and/or automatic way. In case of implementation or partly implementation as software, such software may be adapted to run on suitable computer or computer platform, based on one or more processors. The software may be adapted for use with any suitable operating system such as for example a Windows operating system or Linux operating system. The computing means may comprise a processing means or processor for processing data. According to some embodiments, the processing means or processor may be adapted for determining DNA and/or RNA based on spectral analysis according to any of the methods as described above. Besides a processor, the computing system furthermore may comprise a memory system including for example ROM or RAM, an output system such as for example a CD-rom or DVD drive or means for outputting information over a network. Conventional computer components such as for example a keyboard, display, pointing device, input and output ports, etc also may be included. Data transport may be provided based on data busses. The memory of the computing system may comprise a set of instructions, which, when implemented on the computing system, result in implementation of part or all of the standard steps of the methods as set out above and optionally of the optional steps as set out above. The obtained results may be outputted through an output means such as for example a plotter, printer, display or as output data in electronic format.

Further aspect of embodiments of the present invention encompass computer program products embodied in a carrier medium carrying machine readable code for execution on a computing device, the computer program products as such as well as the data carrier such as dvd or cd-rom or memory device. Aspects of embodiments furthermore encompass the transmitting of a computer program product over a network, such as for example a local network or a wide area network, as well as the transmission signals corresponding therewith.

By way of illustration, embodiments of the present invention not being limited thereto, a number of examples of the effect of buffer and salt contents are discussed below. The latter illustrates how embodiments of the present invention can advantageously be used.

Figure 4:
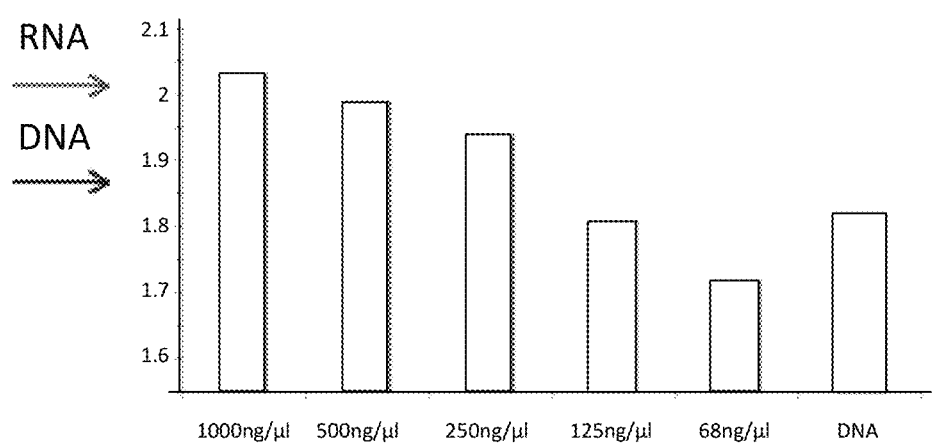
FIG. 4 illustrates measurement results of optical densities of RNA and DNA, illustrating features and advantages of embodiments of the present invention.
Figure 5:
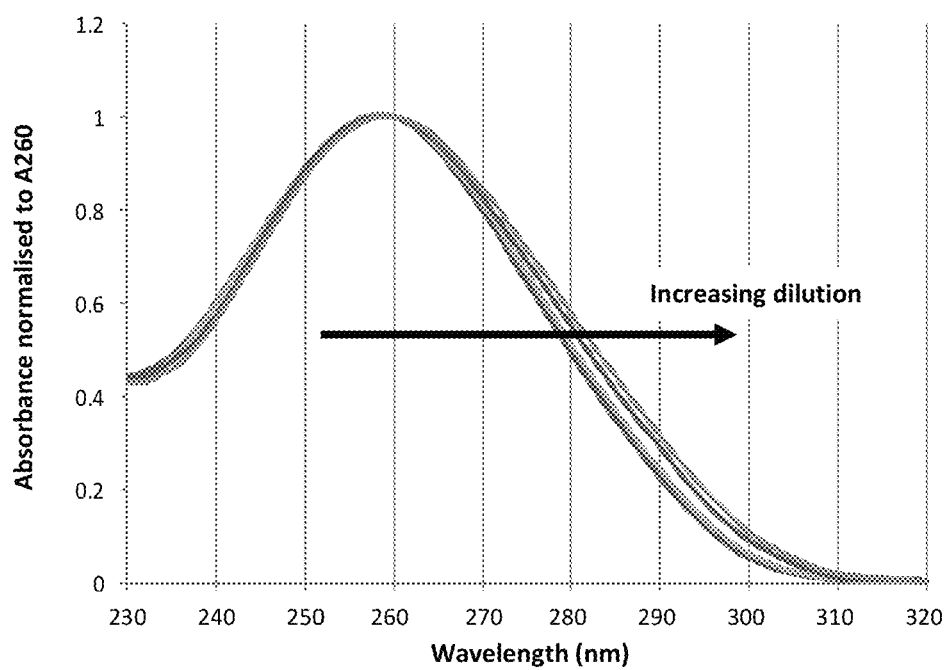
FIG. 5 illustrates an example of the shift of the UV-VIS absorption spectrum towards longer wavelengths upon dilution, as can be compensated for using embodiments of the present invention.

FIG. 4 illustrates the ratio of the absorption at 260 nm and at 280 nm for different RNA concentrations and for DNA, illustrating that based on this ratio the distinction between RNA and DNA cannot unambiguously be made. By diluting in water, a shift of the spectra towards longer wavelengths is typically measured, as can be seen in FIG. 5. Consequently, if not taken into account, the effect of dilution and different buffers and/or salt concentrations on the spectra may result in an erroneous quantification of DNA and/or RNA. Using a deconvolution whereby furthermore the effect of buffers and/or salts are taken into account using a method as described above results in the possibility to accurately determine RNA and DNA content, without being disturbed by shifting and/or deformation effects due to buffers and/or salts. Other experimental results also confirm that an accurate determination of RNA and DNA, especially of RNA, can be performed. Results were obtained for mixed RNA and DNA samples. It was found that, using a method according to an embodiment of the present invention, accurate determination of the ratio of RNA to DNA could be achieved.

The invention claimed is:

1. A method for the automated characterization of a sample comprising at least DNA and/or RNA, the method comprising:
   obtaining a UV-VIS spectroscopic measurement of the sample comprising at least DNA and/or RNA; and
   determining a DNA and/or RNA content in the sample,
   wherein said determining the DNA and/or RNA content in the sample is independent of a buffer and salt content of the sample,
   wherein said determining comprises comparing the UV-VIS spectroscopic measurement of the sample to reference spectral data obtained from a plurality of reference samples, the reference spectral data including spectral information for buffer and/or salt content of the plurality of reference samples, and
   wherein said determining further comprises using reference spectral data from at least two reference samples comprising DNA and/or RNA content and having distinct buffer and/or salt contents.

2. The method according to claim 1, wherein the method further comprises retrieving said reference spectral data including spectral information for the distinct buffer and/or salt contents from a memory.

3. The method according to claim 1, wherein at least part of the reference spectral data is determined based on a method comprising:
   obtaining prior information regarding DNA and/or RNA content and buffer and/or salt content for a plurality of samples having distinct buffer and/or salt content;

obtaining UV-VIS spectrophotometer data for said samples;

defining a number of overlapping components contributing in the UV-VIS spectrophotometer data, the number of overlapping components comprising one or more components assigned to RNA and/or DNA constituents of the one or more samples and the number of overlapping components comprising at least one component that cannot be assigned to known constituents of the one or more samples and that is directly representative of the effect of buffer and/or salt content on the UV-VIS spectrophotometer data for said samples;

using the prior information for the one or more samples regarding their constituents and the UV-VIS spectrophotometer data;

estimating the constituents composition and the component contributions to the UV-VIS spectrophotometer data for the number of components for the one or more samples by minimizing a residue between the UV-VIS spectrophotometer data and a fit based on said constituent composition and said component contributions; and thus obtaining information regarding the one or more components assigned to known constituents of the one or more samples and regarding the at least one component that cannot be assigned to known constituents of the one or more samples and that is directly representative of the effect of the buffer and/or salt content on the UV-VIS spectrophotometer data for said samples.

4. The method according to claim 1, wherein at least part of the reference spectral data is determined based on a method comprising;

obtaining UV-VIS spectrophotometer data for at least two reference samples comprising DNA and/or RNA content and having distinct buffer and/or salt contents;

determining a difference spectrum based on the UV-VIS spectrophotometer data for the at least two reference samples; and determining at least part of the reference spectral data based on said difference spectrum.

5. The method according to claim 1, wherein the reference spectral data is a non-linear curve.

6. The method according to claim 1, wherein the sample comprises RNA and wherein quantifying comprises quantifying an amount of RNA in the sample.

7. The method according to claim 1, wherein the sample comprises an RNA/DNA mixture and wherein the method comprises determining a fraction of RNA in the mixture.

8. A system for the automated characterization of a sample comprising at least DNA and/or RNA, the system comprising:

an input configured to obtain a UV-VIS spectroscopic measurement of the sample comprising at least DNA and/or RNA; and a processor comprising stored instructions configured to determine a DNA and/or RNA content of the sample based on the obtained UV-VIS spectroscopic measurement, the processor being programmed for determining the DNA and/or RNA content of the sample independent of a buffer and salt content of the sample, and said instructions further configured to compare the UV-VIS spectroscopic measurement to reference spectral data obtained from a plurality of reference samples, wherein the reference spectral data includes spectral information for buffer and/or salt content of the plurality of reference samples, and wherein the reference spectral data further includes spectral information for at least two reference samples having distinct buffer and/or salt contents.

9. A non-transitory computer program product storing instructions configured to, if implemented on a processing unit, perform a method for the automated characterization of a sample comprising at least DNA and/or RNA, the method comprising:

obtaining a UV-VIS spectroscopic measurement of the sample comprising at least DNA and/or RNA; and determining a DNA and/or RNA content of the sample, wherein said determining the DNA and/or RNA content of the sample is independent of a buffer and salt content of the sample, wherein said determining comprises comparing the UV-VIS spectroscopic measurement to reference spectral data obtained from a plurality of reference samples, wherein the reference spectral data includes spectral information for buffer and/or salt content of the plurality of reference samples, and wherein the reference spectral data further includes spectral information for at least two reference samples having distinct buffer and/or salt contents.

10. A method for upgrading a spectrophotometer, the method comprising:

storing reference spectral data including spectral information for buffer and/or salt content for a plurality of reference samples on a memory in a processor of the spectrophotometer and installing the computer program product of claim 9 on the spectrophotometer.

\* \* \* \* \*